(12) United States Patent
Manikandan et al.

(10) Patent No.: US 8,598,239 B2
(45) Date of Patent: Dec. 3, 2013

(54) ANDERSON-TYPE HETEROPOLY COMPOUND-BASED CATALYST COMPOSITIONS AND THEIR USE CONVERSION OF SYNTHESIS GAS TO OXYGENATES

(75) Inventors: Palanichamy Manikandan, Pune (IN); David G. Barton, Midland, MI (US); Dean M. Millar, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/825,607

(22) PCT Filed: Sep. 26, 2011

(86) PCT No.: PCT/US2011/053197
§ 371 (c)(1),
(2), (4) Date: Mar. 22, 2013

(87) PCT Pub. No.: WO2012/050804
PCT Pub. Date: Apr. 19, 2012

(65) Prior Publication Data
US 2013/0190411 A1    Jul. 25, 2013

Related U.S. Application Data

(60) Provisional application No. 61/391,735, filed on Oct. 11, 2010.

(51) Int. Cl.
*C07C 27/00* (2006.01)

(52) U.S. Cl.
USPC ........... 518/714; 518/713; 518/715; 518/716; 518/717; 518/719

(58) Field of Classification Search
USPC .......................... 518/713, 714, 715, 717, 719
See application file for complete search history.

(56) References Cited

U.S. PATENT DOCUMENTS

| | | | |
|---|---|---|---|
| 4,210,597 A | 7/1980 | Huang | |
| 4,607,056 A | 8/1986 | Grazioso et al. | |
| 4,616,040 A | 10/1986 | Grazioso et al. | |
| 4,749,724 A | 6/1988 | Quarderer et al. | |
| 4,825,013 A | 4/1989 | Quarderer et al. | |
| 7,923,405 B2* | 4/2011 | Kharas et al. | 502/216 |

FOREIGN PATENT DOCUMENTS

GB    2151616 A    7/1985

OTHER PUBLICATIONS

K. Nomiya et al., in "Anderson-Type Heteropolyanions of Molybdenum (VI) and Tungsten (VI)", Polyhedron, vol. 6, No. 2, pp. 213-218 (1987).
C. Cabello et al., in "Anderson type heteropolyoxomolybdates in catalysis: 1. (NH4)3[CoMo6O24H6]•7H2O/?-Al2O3 as alternative of Co-Mo/?-Al2O3 hydrotreating catalysts", Applied Catalysis A: General 197, pp. 79-86 (2000).
C. I. Cabello et al., in "Catalysts based on RhEL6 heteropolymetallates. Bulk and supported preparation and characterization", Studies in Surface Science and Catalysis, 143, Elsevier Science B.V. pp. 565-572 (2002).
I. L. Botto et al., in "(NH4)6[TeMo6O24]•7H2O Anderson phase as precursor of the TeMo5O16 catalytic phase: thermal and spectroscopic Studies", Materials Chemistry and Physics 47 pp. 37-45 (1997).
T. Liu et al., in "Structures and Catalytic Activity of Pt-Mo Bimetallic Ensembles Derived from a New Planar [PtMo6O24]8—Heteropolyanion Supported on Al2O3 and SiO2", Journal of Catalysis 135, pp. 367-385 (1992).
C. Lamonier et al., in "Molybdocobaltate cobalt salts: New starting materials for hydrotreating catalysts", Applied Catalysis B: Environmental 70, pp. 548-556 (2007).

* cited by examiner

*Primary Examiner* — Jafar Parsa

(57) ABSTRACT

Use a transition metal-containing, Anderson-type heteropoly compound catalyst to convert synthesis gas to an oxygenate, especially an alcohol that contains from one carbon atom to six carbon atoms.

8 Claims, No Drawings

ANDERSON-TYPE HETEROPOLY COMPOUND-BASED CATALYST COMPOSITIONS AND THEIR USE CONVERSION OF SYNTHESIS GAS TO OXYGENATES

This application is a non-provisional application claiming priority from the U.S. Provisional Patent Application No. 61/391,735, filed on Oct. 11, 2010, entitled "ANDERSON-TYPE HETEROPOLY COMPOUND-BASED CATALYST COMPOSITIONS AND THEIR USE CONVERSION OF SYNTHESIS GAS TO OXYGENATES" the teachings of which are incorporated by reference herein, as if reproduced in full hereinbelow.

This invention relates generally to catalyst compositions based upon a Anderson-type structure heteropoly compound and their use in converting synthesis gas (syngas, a mixture of carbon monoxide (CO) and hydrogen ($H_2$)) to oxygenates, especially alcohols that contain from two to six carbon atoms ($C_2$ to $C_6$).

Syngas conversion processes employ a variety of catalysts that, in turn, tend to yield a mixture of products (e.g. hydrocarbons such as ethane and propane and oxygenated hydrocarbons such as methanol, ethanol, propanol and butanol). Those who practice such processes continue to seek improved processes and catalysts which provide a product mixture that favors selectivity to oxygenates over hydrocarbons, with at least some practioners preferring certain oxygenates, such as propanol, over other oxygenates, such as methanol. Such a preference stems, at least in part, from ease of converting $C_2$ to $C_6$ oxygenates to corresponding olefins relative to challenges in converting methanol to an olefin.

Anderson-type heteropoly compounds may be represented by general formula $[A]^{n+}[XM_6O_{24}H_x]^{n-}$ (with X being a heteroatom such as Al, or transition metal such as Co, Ni, Rh, located at the center. A is cation such as $H^+$, $(NH_4^+)$, alkali metal ion, metal ion selected from transition metal ions, M being at least one of Mo and W), and n− is net negative charge of anion part and n+ is net positive charge of the cation. Anderson-type heteropoly compounds are classified into the A-type (x=0) and the B-type (x=6) by the number of attached protons, although some polyanions with x other than 0 or 6 have also been reported.

K. Nomiya et al., in "Anderson-Type Heteropolyanions of Molybdenum (VI) and Tungsten (VI)", *Polyhedron*, Volume 6, Number 2, pages 213-218 (1987), disclose, in part, an investigation of B-type molybdopolyanions, especially those that contain a divalent metal ion (Zn(II), Cu(II), Co(II) or Mn(II)) other than Ni(II). They also investigate mixed Ni(II) polyanions where M in the above formula is a mixture of molybdenum (Mo) and tungsten (W).

C. Cabello et al., in "Anderson type heteropolyoxomolybdates in catalysis: 1. $(NH_4)_3[CoMo_6O_{24}H_6]\cdot 7H_2O/\gamma\text{-}Al_2O_3$ as alternative of $Co\text{—}Mo/\gamma\text{-}Al_2O_3$ hydrotreating catalysts", *Applied Catalysis A: General* 197, pages 79-86 (2000), present teachings about a method of preparing $Co\text{—}Mo/\gamma\text{-}Al_2O_3$ HDS (hydrodesulfurization) catalysts using the $(NH_4)_3[CoMo_6O_{24}H_6]\cdot 7H_2O$ Anderson type heteropolyoxomolybdate supported on $\gamma.Al_2O_3$.

C. I. Cabello et al., in "Catalysts based on $RhMo_6$ heteropolymetallates. Bulk and supported preparation and characterization". *Studies in Surface Science and Catalysis,* 143, Elsevier Science B. V. (2002), pages 565-572, refer to prior research on a series of hexametallates named Anderson $[XM_6O_{24}H_6]^{3-}$ where M=Mo, W or $Mo_{(6-x)}W_x$ and X=Co(III), Rh(III), Fe(III), Mi(II), Cu(II), Fe(VI), etc. that enables design and preparation of a variety of mixed by- or tri-metallic phases that show structural and redox properties and potential use in heterogeneous catalysis applications like hydrotreating and ammoxidation.

I. L. Botto et al., in "$(NH_4)_6[TeMo_6O_{24}]\cdot 7H_2O$ Anderson phase as precursor of the $TeMo_5O_{16}$ catalytic phase: thermal and spectroscopic Studies", *Materials Chemistry and Physics* 47 (1997) pages 37-45, characterize Anderson-type heteropolyanion of formula $[XMo_6O_{24}H_6]^{n-}$ where X is, for example, Te, Fe, Co, Al, Ga, Rh, Ni, or Zn.

T. Liu et al., in "Structures and Catalytic Activity of Pt—Mo Bimetallic Ensembles Derived from a New Planar $[PtMo_6O_{24}]^{8-}$ Heteropolyanion Supported on $Al_2O_3$ and $SiO_2$", *Journal of Catalysis* 135 (1992), pages 367-385, present teachings about the title materials in ethene hydrogenation and ethane hydrogenolysis.

C. Lamonier et al., in "Molybdocobaltate cobalt salts: New starting materials for hydrotreating catalysts", *Applied Catalysis B: Environmental* 70, pages 548-556 (2007) deal with use of Anderson heteropolyanions as alternative starting materials to ammonium heptamolybdate and cobalt nitrate for preparation of hydrotreatment (e.g. hydrodesulfurization of thiophene) oxidic precursors. They teach preparation of ammonium salts of the Anderson molybdocobaltate $((NH_4)_3[CoMo_6O_{24}H_6])$ or molydoaluminate $((NH_4)_3[AlMo_6O_{24}H_6])$.

British Patent (GB) 2 151 616 (Jackson) discloses a method for preparing oxygenated hydrocarbons (e.g. methanol, ethanol and propanol) by contacting syngas at an elevated temperature with a catalyst comprising a Group VIII (Periodic Table of the Elements) metal component (iron (Fe), cobalt (Co), nickel (Ni), Ru, Rh, palladium (Pd), osmium (Os), iridium (Ir), and platinum (Pt), especially rhodium (Rh)) supported on tungsten oxide or molybdenum oxide.

U.S. Pat. No. 4,749,724 (Quarderer et al.) discloses a Fischer-Tropsch reaction to form alcohols from syngas using a catalyst containing at least one element selected from Mo, W and Re in free or combined form, an alkali metal or alkaline earth metal promoter, and, optionally, a support. The catalyst may contain limited quantities of components such as zinc (Zn), copper (Cu) and Co.

In some aspects, this invention is a process for converting synthesis gas to an oxygenate, which process comprises contacting a mixture of hydrogen and carbon monoxide with a transition metal-containing, Anderson-type heteropoly compound catalyst under conditions of temperature, pressure and gas hourly space velocity sufficient to convert said mixture to at least one alcohol wherein the alcohol contains from one carbon atom to six carbon atoms, the catalyst having a structure represented by general formula $(A)_x[M_1Mo_yW_{6-y}]M_2$, wherein A is $H^+$, an ammonium ion $(NH_4)^+$, or an alkali metal ion, $M_1$ is at least one of aluminium, zinc or a transition metal selected from iron, ruthenium, chromium, rhodium, copper, cobalt, nickel, palladium and iridium, $M_2$ is an optional modifier metal that is at least one metal selected from an alkali metal, an alkaline earth metal and a transition metal selected from a group consisting of rhenium, chromium, palladium, cobalt, iridium, nickel, platinum, ruthenium and osmium, x is an integer within a range of from 3 to 4 and y is an integer within a range of from 0 to 6.

The conditions of temperature, pressure and gas hourly space velocity include at least one of a temperature within a range of from 200 degrees Celsius (° C.) to 450° C., a pressure within a range of from 200 psig (1.38 MPa) to 4,000 psig (24.58 MPa) or a gas hourly space velocity is within a range of 300 $hr^{-1}$ to 25,000 $hr^{-1}$.

The mixture of hydrogen and carbon monoxide has a ratio of gaseous hydrogen ($H_2$) to carbon monoxide (CO) within a range of from 10:1 to 1:10.

The above catalysts include an Anderson-type heteropoly compound portion and, optionally, a support portion. When the catalysts include a support portion, the support is present in an amount within a range of from greater than 0 weight percent (wt %) to no more than 95 wt %, preferably from greater than or equal to 40 wt % to no more than (less than or equal to) 90 wt %, in each case based upon total catalyst weight. When the catalysts include a support, the Anderson-type heteropoly compound portion, $(A)_x[M_1Mo_yW_{6-y}]M_2$ (sometimes represented herein simply as "$[M_1Mo_yW_{6-y}]M_2$"), is present in a complementary amount of from at least 5 wt % up to, but not including, 100 wt %, again based on total catalyst weight. The complementary amount is preferably from greater than or equal to 10 wt % to no more than (less than or equal to) 60 wt %, again based on total catalyst weight.

Within the heteropoly compound portion, A is present in an amount within a range of from 0.6 wt % to 40 wt %, preferably from 2 wt % to 25 wt %, $M_1$ is present in an amount within a range of from 1.4 wt % to 16 wt %, preferably from 4 wt % to 10 wt %, Mo is present in an amount within a range of from 0 wt % to 58 wt %, preferably from 12 wt % to 50 wt %, W is present in an amount within a range of from 0 wt % to 73 wt %, preferably from 14 wt % to 45 wt %, and $M_2$, an optional component, is present in an amount within a range of from 0 wt % to 20 wt %, preferably from 2 wt % to 10 wt %, each wt % being based upon total weight of the heteropoly compound.

$M_1$ is one or more metals selected from a group consisting of Rh, Co, Ni, Pd, Zn, Al, Ru, Fe, Pt, Mn, Cr, and Ir. $M_1$ is preferably Rh, Co or Ni. In some aspects, $M_1$ is a combination of cobalt and palladium, cobalt and rhodium, aluminum and rhodium, cobalt and aluminum, copper and cobalt, and zinc and cobalt, and y is 6.

The catalyst can also comprise more than one type of Anderson heteropolyoxo compounds. In some aspects, therefore, the catalyst comprises a mixture of at least two Anderson-type heteropoly compound catalysts, a first wherein $M_1$ is rhodium and a second wherein $M_1$ is selected from cobalt, iridium, copper, nickel, palladium, zinc, aluminum, iron, chromium, and ruthenium.

$M_2$, when present, is a modifier metal that is at least one metal selected from an alkali metal, an alkaline earth metal and a transition metal selected from a group consisting of rhenium (Re), Cr, Pd, Co, Ir, Ni, Pt, Ru, and Os. Alkali metals include sodium, potassium, lithium, rubidium, francium and cesium, with sodium, potassium and lithium being preferred. Alkaline earth metals include calcium, barium, strontium and radium with calcium or barium being preferred. Transition metal choices for $M_2$ are preferably Re, Cr, Pd, Co, Ir and Ni. $M_2$, when present, may, but is not required to, be the same metal as that chosen for $M_1$.

The support portion is preferably selected from silicas ($SiO_2$), zirconias ($ZrO_2$), aluminas ($Al_2O_3$), titanias ($TiO_2$), tungsten oxides ($WO_3$), magnesium oxides (MgO), zinc oxides (ZnO), a mixture of $ZrO_2$ and $Al_2O_3$, also known as zirconia-modified alumina, in either case represented as $ZrO_2$—$Al_2O_3$, magnesium aluminates ($MgAl_2O_4$), zinc aluminates ($ZnAl_2O_4$), and MgO modified supports such as MgO—$Al_2O_3$ and MgO—$SiO_2$.

Anderson-type heteropoly compounds can be prepared according to the methods described by K, Nomiya, et. al. (cited above). These methods relate to the preparation of A-type and B-type Anderson-type heteropoly compounds wherein M=Mo or W, and X is a divalent or trivalent metal ion such as Zn(II) or Al(III). The methods comprise in general preparing molybdo- or tungsto-polyanions by adding an aqueous solution of mewl sulfates aluminas to a boiling aqueous solution of ammonium heptamolybdate hydrate, further evaporating on a steam-bath, followed by filtering the hot solution and cooling.

Arabic numerals designate Examples (Ex) of the present invention and capital alphabetic letters indicate Comparative Examples (Comp Ex or CEx).

EX 1

Dropwise add, with stiffing and at room temperature (nominally 25° C.), 0.5 grams (g) of a 30% aqueous solution of hydrogen peroxide ($H_2O_2$) to an aqueous solution of cobalt sulfate ($CoSO_4.4H_2O$, S. D. Fine, 1.04 g dissolved in 8 milliliters (mL) of water) to form a first solution. Add the first solution, with stirring at 95° C. for 90 minutes, to a second solution of 7.65 g of ammonium heptamolybdate (($NH_4)_6Mo_7O_{24}.4H_2O$, Acros Chemicals) dissolved in 65 mL water) form a third solution. Halt stiffing and allow the third solution to stand overnight. Recover from the third solution, by filtration and drying at a temperature of 80° C., a green, crystalline powder represented as $(NH_4)_3[CoMo_6O_{24}H_6].7H_2O$, an Anderson-type heteropolyoxomolydate referred to herein by a shorthand designation as $[CoMo_6]$.

EX 2

Replicate Ex 1, but substitute an aqueous solution of rhodium nitrate (Fluka, 0.45 g dissolved in 20 mL water) for the first solution and change the second solution to 2.60 g of $(NH_4)_6Mo_7O_{24}.4H_2O$ dissolved in 40 mL water. Recover a yellow, crystalline powder from the third solution. The powder is represented as $(NH_4)_3[RhMo_6O_{24}H_6].7H_2O$, an Anderson-type heteropolyoxomolydate referred to herein by a shorthand designation as $[RhMo_6]$.

EX 3

Replicate Ex 1, but substitute an aqueous solution of aluminum nitrate ($Al(NO_3)_3.9H_2O$, Acros Chemicals, 1.16 g dissolved in 20 mL water) for the first solution and change the second solution to 5.01 g of $(NH_4)_6Mo_7O_{24}.4H_2O$ dissolved in 80 mL water. The powder is represented by a shorthand designation as $[AlMo_6]$.

EX 4

Replicate Ex 1, but substitute an aqueous solution of copper sulfate ($CuSO_4.5H_2O$, S. D. Fine, 1.50 g dissolved in 40 mL water) for the first solution and change the second solution to 10.00 g of $(NH_4)_6Mo_7O_{24}.4H_2O$ dissolved in 160 mL water. Recover a light blue, crystalline powder, represented as $[CuMo_6]$, from the third solution.

EX 5

Replicate Ex 1, but substitute an aqueous solution of palladium chloride ($PdCl_2$, (Acros, 0.55 g dissolved in 20 mL water plus 4 drops of concentrated hydrochloric acid (HCl)) for the first solution and change the second solution to 10.00 g of $(NH_4)_6Mo_7O_{24}.4H_2O$ dissolved in 160 mL water. Recover a yellow, crystalline powder, represented as $[PdMo_6]$, from the third solution.

EX 6

Form a combined solution by mixing an aqueous solution of 2.80 g of $[CoMo_6]$ (from Ex 1) in 25 mL of water with 28.05 g of colloidal silica (34 wt % LUDOX colloidal suspension in deionized water, 158.7 millimoles (mmol) of colloidal silica) with vigorous stirring at room temperature for 90 minutes. Evaporate the combined solution to dryness at 100° C. to yield dried solids, then calcine the dried solids at 350° C. for 4 hr under static air.

Mix, with stirring at room temperature, an aqueous solution of potassium carbonate ($K_2CO_3$ (CDH, 0.29 g dissolved in 20 mL of water)) with 11.01 g of the calcined solids, then evaporate the resulting mix to dryness at 100° C. and calcine the dried mix at 350° C. in static air for 4 hr to yield a catalyst represented as $[CoMo_6]/SiO_2/K$.

Use a high pressure (1500 pounds per square inch gauge (psig) (10.34 megapascals (MPa)) tubular microreactor system to evaluate catalyst activity for converting synthesis gas (syngas) to a mixed alcohol product. Place 1.5 g of the catalyst in the center of a stainless steel reactor (outer diameter (O.D.) of 0.25 inch (0.63 centimeter (cm)) mounted vertically in a furnace. Use thermal mass controllers to transfer syngas (carbon monoxide to hydrogen ($CO:H_2$) ratio of 1:1) from compressed gas cylinders via an activated carbon purifier to the reactor, controlling reactor pressure via an air actuated back pressure regulator located downstream of the reactor. Use an electrically heated aluminum block to control reactor temperature. Before introducing syngas to the reactor, pretreat the catalyst in flowing hydrogen ($H_2$) (150 standard cubic centimeters per minute (s-cm$^3$/min)) at 330° C. for 4 hrs. After pretreatment, lower reactor temperature to 270° C., change the gas flow to 300 s-cm$^3$/min of syngas and then pressurize the reactor to 1500 psig (10.34 MPa).

Analyze products from the reactor by flowing gas phase reactor effluent at ambient pressure (nominally one atmosphere or 0.1 MPa) through a gas sampling valve within a Siemens MAXUM™ gas chromatograph. To avoid condensation of non-volatile products, heat all tubing downstream of the reactor to 160° C. Effect product separation by means of a REOPLEX™ precolumn connected in series with a PORAPAK™ QS column. Quantify effluent from the PORAPAK column using a calibrated flame ionization detector (FID). Summarize results in Table 1 below.

EX 7

Replicate Ex 6, but first combine an aqueous solution of $[PdMo_6]$(from Ex 5) (1.41 g dissolved in 25 mL water)) and an aqueous solution of $[CoMo_6]$(from Ex 1) (1.40 g in 25 mL water) at 90° C. and add the combined solutions to 27.99 g of colloidal silica. Change the $K_2CO_3$ solution to 0.21 g of $K_2CO_3$ dissolved in 20 mL of water and change the amount of calcined powder mixed therewith to 12 g. This Ex 7 produces a catalyst represented as $[PdMo_6][CoMo_6]/SiO_2/K$.

EX 8

Replicate Ex 7, but substitute an aqueous solution of ammonium rhodium molybdate $[RhMo_6]$(from Ex 2) (1.41 g dissolved in 25 mL water) for the ammonium palladium molybdate solution. Change the amount of calcined dried solids to 11 g. This Ex 8 produces a catalyst represented as $[RhMo_6][CoMo_6]/SiO_2/K$.

EX 9

Replicate Ex 8, but substitute the aqueous solution of ammonium aluminum molybdate $[AlMo_6]$ of Ex 3 for the aqueous solution of ammonium cobalt molybdate and change the amount of $[RhMo_6]$ dissolved in 25 mL of water to 1.40 g. This Ex 9 produces a catalyst represented as $[RhMo_6][AlMo_6]/SiO_2/K$.

EX 10

Replicate Ex 7, but substitute an aqueous solution of $[AlMo_6]$(1.41 g dissolved in mL water) for the aqueous solution of ammonium palladium molybdate. This Ex 10 produces a catalyst represented as $[CoMo_6][AlMo_6]/SiO_2/K$.

EXAMPLE 11

Replicate Ex 7, but substitute an aqueous solution of $[CuMo_6]$(from Ex 4), 1.40 g dissolved in 25 mL water) for $[PdMo_6]$ solution. This Ex 11 produces a catalyst represented as $[CuMo_6][CoMo_6]/SiO_2/K$.

EX 12

Replicate Ex 11, but substitute an aqueous solution of ammonium zinc molybdate $((NH_4)_3[ZnMo_6O_{24}H_6]$(1.40 g dissolved in 25 mL water)) for the $[CuMo_6]$ solution. Synthesize $(NH_4)_3[ZnMo_6O_{24}H_6]$ by replicating Ex 4 and substitute zinc sulfate ($ZnSO_4.7H_2O$, S. D. Fine, 1.73 g) for copper sulfate ($CuSO_4.5H_2O$, S. D. Fine, 1.50 g) and the resultant compound is presented as $[ZnMo_6]$. Change the amount of calcined powder mixed with the $K_2CO_3$ solution to 11 g and the amount of $K_2CO_3$ in said solution to 0.19 g. This Ex 12 produces a catalyst represented as $[ZnMo_6][CoMo_6]/SiO_2/K$.

TABLE 1

| Ex | 6 | 7 | 8 | 9 | 10 | 11 | 12 |
|---|---|---|---|---|---|---|---|
| $CO:H_2$ | 1:1 | 1:1 | 1:1 | 1:1 | 1:1 | 1:1 | 1:1 |
| Reaction temperature, ° C. | 339.8 | 340.2 | 339.8 | 340 | 339 | 340 | 340 |
| Reaction pressure, psig/MPa | 1502/ 10.36 | 1502/ 10.36 | 1526/ 10.52 | 1498/ 10.32 | 1502/ 10.36 | 1498/ 10.32 | 1500/ 10.34 |
| GHSV, h$^{-1}$ | 7122 | 6024 | 5647 | 5127 | 6333 | 7067 | 6512 |
| CO conv., mol % | 10.5 | 9.57 | 24.23 | 12.33 | 9.07 | 8.43 | 5 |
| MeOH sel., mol % | 20.07 | 23.6 | 21.4 | 24.6 | 19.4 | 22.5 | 23.6 |
| EtOH sel, mol % | 16.4 | 13.85 | 15.5 | 12.11 | 14.4 | 11.9 | 10.8 |
| PrOH sel, mol % | 7.6 | 7.3 | 8.5 | 5.7 | 6.8 | 5.5 | 4.4 |
| Alcohol sel, mol % | 47 | 47.6 | 49 | 45 | 42.1 | 41.6 | 40 |
| $CH_4$ sel, mol % | 22 | 23.8 | 21.8 | 26.5 | 21.6 | 26.8 | 33 |
| $C_2$ HC sel, mol % | 14.4 | 14.5 | 13.9 | 15.1 | 16.7 | 17.4 | 15.7 |
| HC sel, mol % | 51.4 | 51.4 | 49.8 | 54.2 | 56.5 | 57.8 | 59.5 |
| EtOH prod., g/kg$_{cat}$-h | 68.5 | 46.26 | 130.4 | 52.83 | 47.76 | 36.3 | 21.8 |

TABLE 1-continued

| Ex | 6 | 7 | 8 | 9 | 10 | 11 | 12 |
|---|---|---|---|---|---|---|---|
| PrOH prod., g/kg$_{cat}$-h | 23.7 | 18.3 | 53.45 | 18.35 | 15.88 | 12.7 | 6.7 |
| Alcohol/HC prod. ratio | 1.56 | 1.62 | 1.68 | 1.47 | 1.3 | 1.28 | 1.21 |

MeOH = methanol;
EtOH = ethanol;
PrOH = propanol;
CH$_4$ = methane;
C$_2$ = two carbon atoms; and
HC = hydrocarbon;
sel = selectivity;
conv = conversion;
prod = productivity The data in Table 1 demonstrate that various Anderson heteropoly compound-based catalyst compounds effectively convert syngas to a mixture of alcohols, with that of Ex 8 providing especially effective results.

CEx A

Impregnate 1.8 g of a zirconia-alumina (ZrO$_2$—Al$_2$O$_3$) support at room temperature by dropwise adding thereto, with stirring at 50 rpm for 10 min, an aqueous solution of rhodium nitrate (Rh(NO$_3$)$_3$, (Aldrich, 0.038 g dissolved in 2 mL water)). Dry the impregnated support at 120° C. for 5 hrs, then calcine the dried, impregnated support at 400° C. for 4 hours in static air to yield a catalyst represented as Rh/ZrO$_2$—Al$_2$O$_3$.

Use a high pressure tubular microreactor system to evaluate catalyst performance for converting a feedstream of carbon monoxide, and hydrogen to alcohols. The system includes a stainless steel reactor tube having a length of 14 inches (35.6 centimeters (cm)) and an outside diameter of 0.25 inch (0.64 cm) that is mounted vertically in an electrically heated aluminum block that controls reactor temperature. Place 0.25 g of the catalyst in the center of the reactor tube and place quartz beads at the top and bottom of the tubes. Introduce feedstream gases (CO and H$_2$) to the reactor along with nitrogen (N$_2$) as an internal standard from compressed gas cylinders, using a thermal mass controller to control gas flow rates for each of the feedstream gases and N$_2$. Use an activated carbon purifier to remove any metal carbonyls that may be present in the CO cylinder. Control reactor pressure using an air-actuated back pressure regulator located in a line connected to, but downstream of, the reactor.

Before introducing the feedstream and N$_2$ to the reactor, pretreat the catalyst with flowing H$_2$ (1000 mL/hr) at 330° C. for 2 hrs. After pretreating the catalyst, lower reactor temperature to 280° C., change the gas flowing through the reactor to a mixture of carbon monoxide (CO) and hydrogen (H$_2$) (1:1), and pressurize the reactor to 1000 psig (6.89 megapascals (MPa)). Analyze products from the reactor by flowing reactor effluent through a gas sampling valve within an Agilent gas chromatograph (GC) (model 7890A). Heat tubing between the reactor and the GC to a temperature of 150° C. to 180° C. to minimize condensation of reaction products that are not volatile at lower temperatures. Effect product separation in the GC by flowing reactor effluent through three parallel separation trains: a) a molecular sieve packed column and a HayeSep™ T packed column, (b) PoraBOND™ U capillary column, and (c) a capillary CP Wax separation column. Use the Siemens SIMATIC PCS7 distributed automatic control systems for measurement, control, and safeguarding of the reactor system and summarize analytical results in Table 2.

CEx B

Replicate CEx A, but change the amount of rhodium nitrate in the solution to 0.046 g and substitute a magnesium aluminate (MgAl$_2$O$_4$) support for the ZrO$_2$—Al$_2$O$_3$ support to yield a catalyst represented as Rh/MgAl$_2$O$_4$.

CEx C

Replicate CEx A, but change the amount of rhodium nitrate in the solution to 0.046 g and add to the solution 0.165 g of ammonium heptamolybdate ((NH$_4$)$_6$Mo$_7$O$_2$.2H$_2$O, Aldrich) to yield a catalyst represented as RhMo$_6$ZrO$_2$—Al$_2$O$_3$.

CEx D

Replicate CEx C, but reduce the amount of ammonium heptamolybdate to 0.068 g and add to the solution 0.098 g of ammonium metatungstate (H$_{26}$N$_6$O$_{40}$W$_{12}$, Aldrich,) to yield a catalyst represented as RhMo$_3$W$_3$/ZrO$_2$—Al$_2$O$_3$.

EX 13

Replicate CEx A, but change the support to 0.9 g of gamma-alumina (Aldrich), the aqueous solution to 0.1 g of the [RhMo$_6$] catalyst from Ex 2 in 2 mL of water, the calcination pressure and catalyst performance pressure to that of Ex 1 and the pretreatment time to 3 hours to yield a catalyst represented as [RhMo$_6$]/Al$_2$O$_3$.

Evaluate catalyst performance using a high pressure parallel fixed bed reactor (PFBR) (PFBR System P/N; 132088 from Symyx™ Technologies Inc), a modular reactor composed of three bays, each of which contains 16 reactor tubes. The tubes in each bay are enclosed in a stainless steel bell jar capable of being pressurized with nitrogen (N$_2$) at the same pressure as that used in each reaction. Load reactor tubes with 200 microliters (L) of catalyst, reduce the catalyst in situ at 1500 psig for three hours at 330° C. (heating rate of 5° C. per minute) using a gaseous mixture of 90 volume % (vol %)) percent (vol %) hydrogen (H$_2$) and 10 vol % N$_2$, each vol % being based on total gaseous mixture volume. Cool the catalyst to 280° C.

Test the catalyst at a pressure of 1500 psig, temperatures as shown in Table 3 and GHSV of 6250 h$^{-1}$ using a feed mixture of carbon monoxide (CO) and hydrogen (H$_2$) (1:1 v/v %). Continue testing at 320° C. but at a pressure of 90 bar (9 MPa), then return the pressure to 35 bar (3.5 MPa) and test at 340° C. Evaluate reactor tube effluent using a Siemens process GC. Replicate this catalyst test cycle two additional times and report test results as an average of three test cycles in Table 3.

EX 14

Replicate Ex 13, but change the support to 0.9 g of SiO$_2$ (Aldrich) to yield a catalyst represented as [RhMo$_6$]/SiO$_2$.

EX 15

Replicate Ex 13, but change the support to 0.9 g of $TiO_2$ (Aldrich) to yield a catalyst represented as $[RhMo_6]/TiO_2$.

EX 16

Replicate Ex 13, but change the support to 0.9 g of $ZrO_2$ (Aldrich)) to yield a catalyst represented as $[RhMo_6]/ZrO_2$.

EX 17

Prepare a mixed zirconia-alumina precipitate by adding, at a rate of 5 mL/minute, an aqueous solution of potassium carbonate ($K_2CO_3$ (CDH, 44.08 g, 0.277 mol, dissolved in 250 mL of water)) to a stirred, 70° C. aqueous solution that contains both zirconium nitrate ($ZrO(NO_3)_2$ $2H_2O$ (Aldrich, 1.50 g, 6.49 mmol)) and aluminum nitrate ($Al(NO_3)_3 9H_2O$ (S.D. Fine, 51.75 g, 0.09 mol) dissolved in 1000 mL of water.) After three hours, recover the precipitate by filtration and wash it repeatedly four times with hot water (90° C.). Dry the washed precipitate at 120° C. for 5 hours then calcine the dried precipitate at 450° C. in static air for 4 hours to yield a compound referred as $ZrO_2$—$Al_2O_3$. Washing effectively removes $K_2CO_3$, added as a precipitating agent, from the precipitate.

Replicate Ex 13, but change the substrate to the $ZrO_2$—$Al_2O_3$ compound to yield a compound represented as $[RhMo_6]ZrO_2$—$Al_2O_3$. Summarize results at 1000 psig (6.89 MPa) in Table 2 and at 1500 psig (10.34 MPa) in Tables 3, 4 and 5.

EX 18

Prepare a combined solution by adding an aqueous solution of magnesium nitrate ($Mg(NO_3)_2.6H_2O$ (S.D Fine, 1.03 g, 4 mmol, dissolved in 20 mL of water)) and aluminum nitrate ($Al(NO_3)_3.9H_2O$ (Aldrich, 3.00 g, 8 mmol, dissolved in 30 mL of water)) to an aqueous solution containing urea (S.D. Fine, 4.80 g, 0.08 mol, dissolved in 20 mL of water). Transfer the combined solution to a 100 mL Teflon coated autoclave, seal the autoclave and heat its contents at 180° C. for 20 hours. Cool the autoclave contents to ambient temperature, recover precipitate by filtration, wash the precipitate three times with water. Dry the washed precipitate in an air oven at 100° C. for 1 hour, then calcine the dried precipitate at 700° C. for 4 hours in static air to yield a compound referred to as magnesium aluminate or $MgAl_2O_4$.

Replicate Ex 13, but change the substrate to $MgAl_2O_4$ to yield a compound represented as $[RhMo_6]/ZrO_2$—$Al_2O_3$. Summarize results in Tables 3, 5 and 6.

EX 19

Heat to boiling a combination of molybdenum oxide ($MoO_3$, SD Fine, 0.49 g, 3.41 mmol) and sodium tungstate ($Na_2WO_4.2H_2O$, Chemport, 1.12 g, 3.41 mmol) in 80 mL of water. Dropwise add an aqueous solution of rhodium nitrate (Aldrich, 0.32 g, 1.03 mmol) dissolved in 20 mL of water to the above solution to form a combined mixture, then allow the combined mixture to stand overnight at 80° C. to allow solids to crystallize out of solution. Recrystallize the solids from water two times to yield a compound is represented as $[RhW_3Mo_3]$.

At room temperature, impregnate 0.9 g of the same $MgAl_2O_4$ substrate as in Ex 18 with an aqueous solution of the $[RhW_3Mo_3]$(0.1 g dissolved in 2 mL water), then dry and calcine the impregnated substrate as in Ex 17, save for reducing calcining temperature to 350° C. to yield a compound represented as $[RhW_3Mo_3]/MgAl_2O_4$. Evaluate catalyst performance as in CEx A and report in Table 2. Evaluate catalyst performance as in Ex 13 and summarize results in Table 5.

EX 20

Use the apparatus of CEx A with a modification to allow the feedstream to include ethylene and a modification of the procedure of CEx A to evaluate catalyst performance using the catalyst of Ex 19. The procedural changes are: a) increasing the amount of catalyst to 0.35 g; b) change the feedstream to a mixture of ethylene, CO, $H_2$ and $N_2$ in a respective volumetric ratio of 5:45:45:5; c) change the pressure to which the reactor is pressurized to either 35 bar (3.5 megapascals (MPa) or 90 bar (9.0 MPa) as shown in Table 7 below; and d) use a temperature as shown in Table 7. Summarize results in Table 7.

EX 21

Replicate Ex 19, but change the substrate to mixed zirconia-aluminate prepared as in Ex 17 above to yield a compound represented as $[RhW_3Mo_3]/ZrO_2$—$Al_2O_3$. Evaluate catalyst performance as in Ex 13 and summarize results in Table 5.

EX 22

Add an aqueous solution containing cesium carbonate (Aldrich, 0.09 mmol), sodium carbonate (Aldrich, 0.09 mmol) and lithium carbonate (Aldrich, 0.09 mmol) dissolved in 200 µL of water) to 200 milligrams (mg) of $[RhMo_6]/MgAl_2O_4$ prepared as in Ex 18 to form a modified compound. Calcine the modified compound at 350° C. for four hours in static air to yield a compound represented as $[RhMo_6]$—Cs—Na—Li/$MgAl_2O_4$. Evaluate catalyst performance as in Ex 17 at 1000 psig (6.89 MPa) and summarize results in Table 2 and at 1500 psig (10.34 MPa) and summarize results in Table 6.

EX 23

Replicate Ex 22, but change the aqueous solution to potassium carbonate (Aldrich, 0.03 mmol dissolved in 200 µL of water) to yield a compound represented as $[RhMo_6]$-K/$MgAl_2O_4$, evaluate only at 1500 psig (10.34 MPa) and summarize results in Table 6.

EX 24

Replicate Ex 23, but change the aqueous solution lithium carbonate (Aldrich, 0.09 mmol) dissolved in 200 µL of water) to yield a compound represented as $[RhMo_6]$—Li/$MgAl_2O_4$ and summarize results in Table 6.

EX 25

At room temperature, add an aqueous solution of cobalt sulfate ($CoSO_4.4H_2O$ (S.D. Fine, 1.04 g, 3.7 mmol, dissolved in 8 mL of water)) to 30% $H_2O_2$(Ran Kem, 0.5 g) to form a first solution Add, with stirring, an aqueous solution of ammonium molybdate (($NH_4)_6Mo_7O_{24}.4H_2O$) (SD Fine, 7.65 g, 6.2 mmol, in 65 mL of water) to the first solution. Recover a crystalline material, $[CoMo_6]$, as in Ex 19 above.

At room temperature, impregnate 0.9 g of $ZrO_2$—$Al_2O_3$ with an aqueous solution containing 0.05 g of the $[RhMo_6]$ from Ex 2 and 0.05 g of the [CoMo$_6$] prepared in this example, both dissolved in 1 mL of water. Dry and calcine the impregnated material as in Ex 19 to yield a compound designated as [RhMo$_6$][CoMo$_6$]/ZrO$_2$—Al$_2$O$_3$. Evaluate catalyst performance at 1500 psig (10.34 MPa) and a gas hourly space velocity (GHSV) of 7000 reciprocal hours (h$^{-1}$), and summarize analytical results in Table 4 below.

EX 26

Replicate Ex 25, but substitute preparation of a chromium molybdenum [CrMo$_6$] crystalline material for preparation of the [CoMo$_6$] material. The first solution is an aqueous solution of chromium sulfate (Cr$_2$(SO$_4$)$_3$.4H$_2$O (CDH, 1.44 g, 3.1 mmol, dissolved in 20 mL of water).) Add the first solution, with stirring, to an aqueous solution of (NH$_4$)$_6$Mo$_7$O$_{24}$.4H$_2$O, SD Fine, 5.20 g, 4.2 mmol, in 80 mL of water). Recover a crystalline material [CrMo$_6$] as in Ex 19 above. Replication yields a compound designated as [RhMo$_6$][CrMo$_6$]/ZrO$_2$—Al$_2$O$_3$. Summarize analytical results in Table 4 below.

EX 27

Replicate Ex 25, but substitute preparation of an iridium molybdenum [IrMo$_6$] material for preparation of the [CoMo$_6$] material. The first solution is an aqueous solution of iridium chloride (IrCl$_3$, S.D. Fine, 0.6306 g, 1.888 mmol, dissolved in 10 mL of water). Add the first solution, with stirring, to an aqueous solution of (NH$_4$)$_6$Mo$_7$O$_{24}$.4H$_2$O, SD Fine, 2 g, 1.62 mmol, in 40 mL of water). Recover a crystalline material referred to as [IrMo$_6$] using the procedure detailed in Ex 19 above. Replication yields a compound designated as [RhMo$_6$][IrMo$_6$]/ZrO$_2$—Al$_2$O$_3$. Summarize analytical results in Table 4 below.

EX 28

Replicate Ex 25, but substitute preparation of a nickel molybdenum [NiMo$_6$] material for preparation of the [CoMo$_6$] material. The first solution is an aqueous solution of nickel sulfate (NiSO$_4$.4H$_2$O (S.D. Fine, 1.14 g, 7.40 mmol, dissolved in 20 mL of water).) Add the first solution, with stirring, to an aqueous solution of (NH$_4$)$_6$Mo$_7$O$_{24}$.4H$_2$O (SD Fine, 7.83 g, 6.34 mmol, in 100 mL of water). Recover a crystalline material referred to as [NiMo$_6$] using the procedure detailed in Ex 19 above. Replication yields a compound designated as [RhMo$_6$][NiMo$_6$]/ZrO$_2$—Al$_2$O$_3$. Summarize analytical results in Table 4 below.

EX 29

Replicate Ex 25, but substitute preparation of a palladium molybdenum [PdMo$_6$] material for preparation of the [CoMo$_6$] material. The first solution is an aqueous solution of palladium chloride (PdCl$_2$ (Aldrich, 0.5497 g, 3.1 mmol, dissolved in 20 mL of water).) Add the first solution, with stirring, to an aqueous solution of (NH$_4$)$_6$Mo$_7$O$_{24}$.4H$_2$O (SD Fine, 5.19 g, 4.2 mmol, in 80 mL of water). Recover a crystalline material referred to as [PdMo$_6$] using the procedure detailed in Ex 19 above. Replication yields a compound designated as [RhMo$_6$][PdMo$_6$]/ZrO$_2$—Al$_2$O$_3$. Summarize analytical results in Table 4 below.

EX 30

Combine, with stirring, an aqueous solution of rhenium chloride (ReCl$_3$ (Aldrich, 0.08 g, dissolved in 6 mL of water)) and 1 g of ZrO$_2$—Al$_2$O$_3$. Evaporate solvent from the combination using a rotavap to leave a solid residue. Dry and calcine as in Ex 17 to yield a support designated as Re/ZrO$_2$—Al$_2$O$_3$.

Dropwise add an aqueous solution of 0.05 g of the [RhMo$_6$] from Ex 2 in 6 mL of water to the support, then dry and calcine the support as in Ex 19 to yield a compound designated as [RhMo$_6$]Re/ZrO$_2$—Al$_2$O$_3$. Summarize analytical results in Table 4 below.

EX 31

At room temperature (25° C.), stir together an aqueous solution of rhodium chloride (RhCl$_3$ (Aldrich, 0.20 g, 0.78 mmol, dissolved in 10 mL of water)) and an aqueous solution of ammonium meta-tungstate, ((NH$_4$)$_6$W$_2$O$_{41}$.xH$_2$O, SD Fine, 1.1457 g, 0.3876 mmol, in 50 mL of water). Recover a crystalline material referred to as [RhW$_6$] using the procedure detailed in Ex 19 above.

At room temperature, impregnate 0.9 g of the same MgAl$_2$O$_4$ substrate as in Ex 18 with an aqueous solution of the [RhW$_6$](0.1 g dissolved in 2 mL water), dry the impregnated substrate at 120° C. for 5 hours, then calcine the dried, impregnated substrate at 350° C. in static air for 4 hours to yield a compound represented as [RhW$_6$]/MgAl$_2$O$_4$. Evaluate catalyst performance as described above at 1500 psig (10.34 MPa) and summarize results in Table 5 below.

EX 32

Replicate Ex 20, but use the catalyst from Ex 31. Summarize results in Table 7 below.

EX 33

Replicate Ex 31, but change the substrate to the mixed zirconia-aluminate prepared as in Ex 17 above to yield a compound represented as [RhW$_6$]/ZrO$_2$—Al$_2$O$_3$. Summarize catalyst evaluation results in Table 5 below.

EX 34

Replicate Ex 25, but substitute MgAl$_2$O$_4$ for ZrO$_2$—Al$_2$O$_3$, and substitute preparation of iron molybdenum [FeMo$_6$] crystalline material for preparation of the [CoMo$_6$] material. The first solution is an aqueous solution of ferric ammonium sulfate (NH$_4$Fe(SO$_4$)$_2$.12H$_2$O (Aldrich, 1.5 g, 3.1 mmol, dissolved in 20 mL of water)). Add the first solution, with stirring, to an aqueous solution of (NH$_4$)$_6$Mo$_7$O$_{24}$.4H$_2$O (SD Fine, 5.20 g, 4.2 mmol, in 80 mL of water). Recover a crystalline material referred to as [FeMo$_6$] using the procedure detailed in Ex 19 above. Replication yields a compound designated as [RhMo$_6$][FeMo$_6$]/MgAl$_2$O$_4$. Summarize analytical results in Table 4 below.

EX 35

Replicate Ex 20, but use the catalyst from Ex 34. Summarize results in Table 7 below.

TABLE 2

| Catalyst | Ex. No. | Temp °C. | CO Conv % | S(Alc) % | S(p-ROH) % | S(HC) % |
|---|---|---|---|---|---|---|
| Rh/ZrO$_2$—Al$_2$O$_3$ | CEx A | 300 | 0.48 | 18.89 | 2.30 | 81.11 |
| Rh/ZrO$_2$—Al$_2$O$_3$ | CEx A | 320 | 0.99 | 11.79 | 1.09 | 88.21 |
| RhMo/ZrO$_2$—Al$_2$O$_3$ | CEx C | 300 | 1.31 | 46.79 | 8.02 | 53.21 |
| RhMo/ZrO$_2$—Al$_2$O$_3$ | CEx C | 320 | 2.41 | 31.89 | 6.41 | 68.11 |
| RhMo/ZrO$_2$—Al$_2$O$_3$ | CEx C | 340 | 6.83 | 14.18 | 2.74 | 85.82 |
| [RhMo$_6$]/ZrO$_2$—Al$_2$O$_3$ | Ex 17 | 300 | 4.23 | 55.90 | 8.87 | 44.10 |
| [RhMo$_6$]/ZrO$_2$—Al$_2$O$_3$ | Ex 17 | 320 | 8.65 | 36.66 | 6.66 | 63.34 |
| [RhMo$_6$]/ZrO$_2$—Al$_2$O$_3$ | Ex 17 | 340 | 12.99 | 17.69 | 2.97 | 82.31 |
| Rh/MgAl$_2$O$_4$ | CEx. B | 300 | 0.60 | 22.91 | 1.82 | 77.09 |
| Rh/MgAl$_2$O$_4$ | CEx. B | 320 | 1.07 | 19.28 | 1.59 | 80.72 |
| RhMo$_3$W$_3$/MgAl$_2$O$_4$ | CEx D | 300 | 1.39 | 73.40 | 7.39 | 26.60 |
| RhMo$_3$W$_3$/MgAl$_2$O$_4$ | CEx D | 320 | 2.63 | 67.33 | 7.42 | 32.67 |
| RhMo$_3$W$_3$/MgAl$_2$O$_4$ | CEx. D | 340 | 6.31 | 50.67 | 7.15 | 49.33 |
| [RhW$_3$Mo$_3$]/MgAl$_2$O$_4$ | Ex 19 | 300 | 1.15 | 70.75 | 11.83 | 29.25 |
| [RhW$_3$Mo$_3$]/MgAl$_2$O$_4$ | Ex 19 | 320 | 2.10 | 62.81 | 13.77 | 37.19 |
| [RhW$_3$Mo$_3$]/MgAl$_2$O$_4$ | Ex 19 | 340 | 5.60 | 53.39 | 13.50 | 46.61 |

S(Alc) = selectivity to total alcohols,
S(HC) = selectivity to total hydrocarbons,
S(p-ROH) = selectivity to primary alcohols (ethanol + propanol). Each selectivity is expressed as $CO_2$— free value.

The data in Table 2 compare the performance of [RhMo$_6$] Anderson heteropoly compound-based catalysts with Rh and Rh—Mo containing catalysts that have Rh or Rh and Mo contents equal to those of the [RhMo$_6$] catalysts. With the ZrO$_2$—Al$_2$O$_3$ support, the [RhMo$_6$] based catalyst of Ex 17 provides greater CO conversion and selectivity to both alcohols in general and primary alcohols in particular than the Rh catalysts of CEx A or the RhMo catalysts of CEx C. With the MgAl$_2$O$_4$ support, the [RhW$_3$Mo$_3$] based catalyst of Ex 19 performs much better results in terms of the measured parameters than the Rh catalyst of CEx B and better results in terms of selectivity to primary alcohols than the RhMo$_3$W$_3$ catalyst of CEx D.

TABLE 3

| Catalyst | Ex. No | Temp °C. | CO conv % | S(Alc) % | S(p-ROH) % | S(HC) % | p-ROH/HC |
|---|---|---|---|---|---|---|---|
| [RhMo$_6$]/Al$_2$O$_3$ | Ex 13 | 300 | 5.20 | 10.66 | 0.00 | 37.20 | 0.00 |
| [RhMo$_6$]/Al$_2$O$_3$ | Ex 13 | 320 | 10.16 | 7.43 | 0.41 | 57.16 | 0.01 |
| [RhMo$_6$]/Al$_2$O$_3$ | Ex 13 | 340 | 17.32 | 4.28 | 0.00 | 78.85 | 0.00 |
| [RhMo$_6$]/MgAl$_2$O$_4$ | Ex 18 | 300 | 3.05 | 81.40 | 18.90 | 13.72 | 1.38 |
| [RhMo$_6$]/MgAl$_2$O$_4$ | Ex 18 | 320 | 6.16 | 73.66 | 20.16 | 20.81 | 0.97 |
| [RhMo$_6$]/MgAl$_2$O$_4$ | Ex 18 | 340 | 10.60 | 59.57 | 18.30 | 34.13 | 0.54 |
| [RhMo$_6$]/SiO$_2$ | Ex 14 | 300 | 7.22 | 22.67 | 6.27 | 73.79 | 0.08 |
| [RhMo$_6$]/SiO$_2$ | Ex 14 | 320 | 16.84 | 11.10 | 2.11 | 85.93 | 0.02 |
| [RhMo$_6$]/SiO$_2$ | Ex 14 | 340 | 35.23 | 3.97 | 0.51 | 93.87 | 0.01 |
| [RhMo$_6$]/ZrO$_2$—Al$_2$O$_3$ | Ex 17 | 300 | 3.87 | 65.70 | 34.71 | 23.97 | 1.45 |
| [RhMo$_6$]/ZrO$_2$—Al$_2$O$_3$ | Ex 17 | 320 | 9.53 | 58.90 | 33.59 | 33.59 | 1.00 |
| [RhMo$_6$]/ZrO$_2$—Al$_2$O$_3$ | Ex 17 | 340 | 16.97 | 50.94 | 28.47 | 42.54 | 0.67 |
| [RhMo$_6$]/TiO$_2$ | Ex 15 | 300 | 19.59 | 28.88 | 3.90 | 60.78 | 0.06 |
| [RhMo$_6$]/TiO$_2$ | Ex 15 | 320 | 32.37 | 12.23 | 1.31 | 75.85 | 0.02 |
| [RhMo$_6$]/TiO$_2$ | Ex 15 | 340 | 56.91 | 5.14 | 0.34 | 87.60 | 0.00 |
| [RhMo$_6$]/ZrO$_2$ | Ex 16 | 300 | 5.19 | 28.94 | 15.75 | 50.18 | 0.31 |
| [RhMo$_6$]/ZrO$_2$ | Ex 16 | 320 | 6.95 | 32.60 | 18.49 | 54.01 | 0.34 |
| [RhMo$_6$]/ZrO$_2$ | Ex 16 | 340 | 6.93 | 34.17 | 19.72 | 56.19 | 0.35 |

S(Alc) = selectivity to total alcohols,
S(HC) = selectivity to total hydrocarbons,
S(p-ROH) = selectivity to primary alcohols (ethanol + propanol). Each selectivity is expressed as $CO_2$— free value.

The data in Table 3 show that selectivity to primary alcohols is much better with modified supports such as MgAl$_2$O$_4$ and ZrO$_2$—Al$_2$O$_3$ (Ex 17 and 18) than with conventional supports like Al$_2$O$_3$ (Ex 13), SiO$_2$ (Ex 14), ZrO$_2$ (Ex 16) and TiO$_2$ (Ex 15)

TABLE 4

Experiments with Mixed Anderson

| Catalyst | Ex | Temp | CO conv | S(Alc) | S(p-ROH) | S(HC) | S(p-ROH/HC) |
|---|---|---|---|---|---|---|---|
| [RhMo$_6$]/ZrO$_2$—Al$_2$O$_3$ | 17 | 300 | 3.87 | 65.70 | 34.71 | 23.97 | 1.45 |
| [RhMo$_6$]/ZrO$_2$—Al$_2$O$_3$ | 17 | 320 | 9.53 | 58.90 | 33.59 | 33.59 | 1.00 |
| [RhMo$_6$]/ZrO$_2$—Al$_2$O$_3$ | 17 | 340 | 16.97 | 50.94 | 28.47 | 42.54 | 0.67 |
| [RhMo$_6$][CrMo$_6$]/ZrO$_2$—Al$_2$O$_3$ | 26 | 320 | 1.74 | 38.68 | 18.87 | 38.68 | 0.49 |
| [RhMo$_6$][CrMo$_6$]/ZrO$_2$—Al$_2$O$_3$ | 26 | 340 | 3.99 | 39.18 | 19.78 | 47.76 | 0.41 |
| [RhMo$_6$][PdMo$_6$]/ZrO$_2$—Al$_2$O$_3$ | 29 | 320 | 2.31 | 43.14 | 15.03 | 35.29 | 0.43 |
| [RhMo$_6$][PdMo$_6$]/ZrO$_2$—Al$_2$O$_3$ | 29 | 340 | 6.21 | 41.15 | 19.01 | 45.83 | 0.41 |

TABLE 4-continued

Experiments with Mixed Anderson

| Catalyst | Ex | Temp | CO conv | S(Alc) | S(p-ROH) | S(HC) | S(p-ROH/HC) |
|---|---|---|---|---|---|---|---|
| $[RhMo_6][CoMo_6]/ZrO_2$—$Al_2O_3$ | 25 | 300 | 1.80 | 75.26 | 39.18 | 22.68 | 1.73 |
| $[RhMo_6][CoMo_6]/ZrO_2$—$Al_2O_3$ | 25 | 320 | 3.86 | 61.98 | 33.88 | 31.40 | 1.08 |
| $[RhMo_6][CoMo_6]/ZrO_2$—$Al_2O_3$ | 25 | 340 | 8.62 | 55.03 | 27.43 | 39.06 | 0.70 |
| $[RhMo_6][NiMo_6]/ZrO_2$—$Al_2O_3$ | 28 | 300 | 1.93 | 71.94 | 33.09 | 23.02 | 1.44 |
| $[RhMo_6][NiMo_6]/ZrO_2$—$Al_2O_3$ | 28 | 320 | 4.02 | 62.72 | 30.47 | 32.97 | 0.92 |
| $[RhMo_6][NiMo_6]/ZrO_2$—$Al_2O_3$ | 28 | 340 | 7.68 | 50.95 | 24.71 | 44.30 | 0.56 |
| $[RhMo_6][IrMo_6]/ZrO_2$—$Al_2O_3$ | 27 | 320 | 1.77 | 41.44 | 22.52 | 41.44 | 0.54 |
| $[RhMo_6][IrMo_6]/ZrO_2$—$Al_2O_3$ | 27 | 340 | 3.40 | 39.91 | 21.49 | 46.93 | 0.46 |
| $[RhMo_6]Re/ZrO_2$—$Al_2O_3$ | 30 | 320 | 1.84 | 52.21 | 24.78 | 43.36 | 0.57 |
| $[RhMo_6]Re/ZrO_2$—$Al_2O_3$ | 30 | 300 | 0.62 | 37.04 | 11.11 | 44.44 | 0.25 |
| $[RhMo_6]Re/ZrO_2$—$Al_2O_3$ | 30 | 340 | 4.10 | 49.44 | 25.84 | 45.69 | 0.57 |
| $[RhMo_6][FeMo_6]/MgAl_2O_4$ | 34 | 300 | 1.63 | 83.84 | 14.14 | 6.57 | 2.15 |
| $[RhMo_6][FeMo_6]/MgAl_2O_4$ | 34 | 320 | 3.25 | 75.00 | 15.14 | 10.92 | 1.39 |
| $[RhMo_6][FeMo_6]/MgAl_2O_4$ | 34 | 340 | 4.63 | 59.13 | 14.14 | 23.91 | 0.59 |

S(Alc) = selectivity to total alcohols,
S(HC) = selectivity to total hydrocarbons,
S(p-ROH) = selectivity to primary alcohols (ethanol + propanol). Each selectivity is expressed as $CO_2$— free value.

The data in Table 4 show that one may replace part of the $[RhMo_6]$ with a non-Rh Anderson type precursor such as $[CrMo_6]$(Ex 26), $[NiMo_6]$(Ex 28), $[CoMo_6]$(Ex 25), $[PdMo_6]$ (Ex 29) or $[IrMo_6]$(Ex 27) or modify the $[RhMo_6]$ with a metal such as Re (Ex 30), in each case reducing catalyst cost by eliminating some Rh, an increasingly expensive and decreasingly available metal, with some tradeoff in catalyst performance. Ex 34 suggests that mixed Anderson complexes supported on materials other than $Al_2O_3$ also provide satisfactory results.

TABLE 5

Mo—W mixed Anderson Precursors

| Catalyst | Ex. No | Temp | CO conv | S(Alc) | S(p-ROH) | S(HC) | S(p-ROH)/S(HC) ratio |
|---|---|---|---|---|---|---|---|
| $[RhMo_6]/MgAl_2O_4$ | 18 | 320 | 5.79 | 74.74 | 19.42 | 19.93 | 0.97 |
| $[RhMo_6]/MgAl_2O_4$ | 18 | 340 | 10.60 | 59.57 | 18.30 | 34.13 | 0.54 |
| $[RhMo_6]/ZrO_2$—$Al_2O_3$ | 17 | 320 | 9.53 | 58.90 | 33.59 | 33.59 | 1.00 |
| $[RhMo_6]/ZrO_2$—$Al_2O_3$ | 17 | 340 | 16.97 | 50.94 | 28.47 | 42.54 | 0.67 |
| $[RhW_3Mo_3]/MgAl_2O_4$ | 19 | 320 | 8.96 | 71.70 | 33.68 | 19.30 | 1.75 |
| $[RhW_3Mo_3]/MgAl_2O_4$ | 19 | 340 | 21.81 | 60.04 | 31.15 | 33.00 | 0.94 |
| $[RhMo_3W_3]/ZrO_2$—$Al_2O_3$ | 21 | 320 | 1.94 | 10.28 | 2.80 | 57.94 | 0.05 |
| $[RhMo_3W_3]/ZrO_2$—$Al_2O_3$ | 21 | 340 | 4.82 | 28.32 | 16.78 | 55.24 | 0.30 |
| $[RhW_6]/MgAl_2O_4$ | 31 | 320 | 0.90 | 44.90 | 20.41 | 22.45 | 0.91 |
| $[RhW_6]/MgAl_2O_4$ | 31 | 340 | 1.94 | 37.68 | 22.71 | 34.30 | 0.66 |
| $[RhW_6]/ZrO_2$—$Al_2O_3$ | 33 | 340 | 3.09 | 16.58 | 8.54 | 69.35 | 0.12 |

S(Alc) = selectivity to total alcohols,
S(HC) = selectivity to total hydrocarbons,
S(p-ROH) = selectivity to primary alcohols (ethanol + propanol). Each selectivity is expressed as $CO_2$— free value.

The data in Table 5 show that, while all Ex provide satisfactory results, a combination of a mixed metal Anderson-type heteropoly compound compound-based catalyst compositions and a $MgAl_2O_4$ support (Ex 19) provide unexpectedly superior results relative to the other combinations shown in Table 5.

TABLE 6

Effect of Alkali addition

| Catalyst | Ex. No | Temp °C. | CO conv % | S(Alc) % | S(p-ROH) % | S(HC) % | S(p-ROH)/S(HC) ratio |
|---|---|---|---|---|---|---|---|
| $[RhMo_6]/MgAl_2O_4$ | 18 | 300 | 3.05 | 81.40 | 18.90 | 13.72 | 1.38 |
| $[RhMo_6]/MgAl_2O_4$ | 18 | 320 | 6.16 | 73.66 | 20.16 | 20.81 | 0.97 |
| $[RhMo_6]/MgAl_2O_4$ | 18 | 340 | 10.60 | 59.57 | 18.30 | 34.13 | 0.54 |
| $[RhMo_6]$—$K/MgAl_2O_4$ | 23 | 300 | 2.19 | 83.25 | 30.46 | 13.20 | 2.31 |
| $[RhMo_6]$—$K/MgAl_2O_4$ | 23 | 320 | 4.32 | 70.43 | 30.43 | 26.09 | 1.17 |

TABLE 6-continued

Effect of Alkali addition

| Catalyst | Ex. No | Temp °C. | CO conv % | S(Alc) % | S(p-ROH) % | S(HC) % | S(p-ROH)/S(HC) ratio |
|---|---|---|---|---|---|---|---|
| [RhMo$_6$]—K/MgAl$_2$O$_4$ | 23 | 340 | 7.60 | 57.77 | 26.50 | 36.93 | 0.72 |
| [RhMo$_6$]—Li/MgAl$_2$O$_4$ | 24 | 300 | 2.76 | 91.26 | 16.18 | 4.53 | 3.57 |
| [RhMo$_6$]—Li/MgAl$_2$O$_4$ | 24 | 320 | 4.53 | 86.64 | 17.46 | 9.05 | 1.93 |
| [RhMo$_6$]—Li/MgAl$_2$O$_4$ | 24 | 340 | 7.72 | 70.63 | 20.26 | 24.67 | 0.82 |
| [RhMo$_6$]—Cs—Na—Li/MgAl$_2$O$_4$ | 22 | 300 | 1.70 | 89.08 | 23.56 | 6.32 | 3.73 |
| [RhMo$_6$]—Cs—Na—Li/MgAl$_2$O$_4$ | 22 | 320 | 4.22 | 75.34 | 27.95 | 20.55 | 1.36 |
| [RhMo$_6$]—Cs—Na—Li/MgAl$_2$O$_4$ | 22 | 340 | 7.66 | 61.29 | 25.98 | 33.28 | 0.78 |

S(Alc) = selectivity to total alcohols,
S(HC) = selectivity to total hydrocarbons,
S(p-ROH) = selectivity to primary alcohols (ethanol + propanol). Each selectivity is expressed as CO$_2$— free value.

The data in Table 6 show that an alkali metal modification (Ex 22-24) leads to an increase in selectivity to alcohol or an increase in selectivity to primary alcohols relative to the same catalyst absent an alkali metal modification (Ex 18). Even without the alkali metal modification, the data for Ex 18 are satisfactory.

TABLE 7

Effect of additional ethylene co-feed

| Catalyst | Ex No | Temp °C. | Press. (MPa) | Ethylene conv (%) | CO conv (%) | S Propanol (%) | S Propanal (%) | S Ethane (%) | S CO$_2$ (%) |
|---|---|---|---|---|---|---|---|---|---|
| [RhMo$_3$W$_3$]/MgAl$_2$O$_4$ | 20 | 260 | 3.5 | 79.48 | 5.21 | 53.26 | 7.11 | 35.78 | 0.65 |
| [RhMo$_3$W$_3$]/MgAl$_2$O$_4$ | 20 | 280 | 3.5 | 81.88 | 5.49 | 47.48 | 11.92 | 36.78 | 0.80 |
| [RhMo$_3$W$_3$]/MgAl$_2$O$_4$ | 20 | 300 | 3.5 | 97.89 | 6.84 | 44.95 | 1.88 | 42.05 | 2.81 |
| [RhMo$_3$W$_3$]/MgAl$_2$O$_4$ | 20 | 300 | 9.0 | 94.61 | 8.49 | 59.73 | 2.14 | 29.32 | 2.39 |
| [RhMo$_6$][FeMo$_6$]/MgAl$_2$O$_4$ | 35 | 260 | 3.5 | 56.06 | 2.51 | 46.00 | 2.32 | 49.53 | 0.44 |
| [RhMo$_6$][FeMo$_6$]/MgAl$_2$O$_4$ | 35 | 280 | 3.5 | 69.57 | 2.87 | 40.87 | 2.26 | 54.31 | 0.44 |
| [RhMo$_6$][FeMo$_6$]/MgAl$_2$O$_4$ | 35 | 300 | 3.5 | 84.35 | 4.31 | 35.24 | 2.07 | 58.96 | 0.69 |
| [RhMo$_6$][FeMo$_6$]/MgAl$_2$O$_4$ | 35 | 300 | 9.0 | 88.03 | 4.88 | 42.26 | 1.43 | 51.85 | 1.22 |
| [RhW$_6$]/MgAl$_2$O$_4$ | 32 | 260 | 3.5 | 51.67 | 2.75 | 11.73 | 45.56 | 41.54 | 0.22 |
| [RhW$_6$]/MgAl$_2$O$_4$ | 32 | 280 | 3.5 | 70.21 | 3.56 | 17.06 | 35.35 | 45.98 | 0.25 |
| [RhW$_6$]/MgAl$_2$O$_4$ | 32 | 300 | 3.5 | 90.37 | 4.31 | 24.06 | 20.99 | 52.08 | 0.44 |
| [RhW$_6$]/MgAl$_2$O$_4$ | 32 | 300 | 9.0 | 94.49 | 6.13 | 32.37 | 20.48 | 43.52 | 0.61 |

S means selectivity

The data in Table 7 show that Anderson-type heteropoly compound based catalysts are efficient for a feed that contains ethylene in addition to carbon monoxide and hydrogen.

What is claimed is:

1. A process for converting synthesis gas to an oxygenate, which process comprises contacting a mixture of hydrogen and carbon monoxide with a transition metal-containing, Anderson-type heteropoly compound catalyst under conditions of temperature, pressure and gas hourly space velocity sufficient to convert said mixture to at least one alcohol wherein the alcohol contains from one carbon atom to six carbon atoms, the catalyst having a structure represented by general formula $(A)_x[M_1Mo_yW_{6-y}]M_2$, wherein A is H$^+$, an ammonium ion, or an alkali metal ion, $M_1$ is at least one of aluminum, zinc or a transition metal selected from iron, ruthenium, chromium, rhodium, copper, cobalt, nickel, palladium and iridium, $M_2$ is an optional modifier that is at least one metal selected from an alkali metal, an alkaline earth metal and a transition metal selected from a group consisting of rhenium, chromium, palladium, nickel, iridium and cobalt, x is an integer within a range of from 3 to 4 and y is an integer within a range of from 0 to 6.

2. The process of claim 1, wherein the catalyst comprises a mixture of at least two Anderson-type heteropoly compound catalysts, a first wherein $M_1$ is rhodium and a second wherein $M_1$ is selected from cobalt, iridium, copper, nickel, palladium, zinc, aluminum, iron, chromium, and ruthenium.

3. The process of claim 1, wherein the catalyst further comprises at least one catalyst support selected from silicas, aluminas, titanias, tungsten oxides, zirconias, magnesias, zinc oxides or mixtures thereof, and modified supports selected from zirconia-modified silicas and aluminas, magnesium aluminates, zinc aluminates, and magnesium modified silicas and aluminas.

4. The process of claim 1, wherein the conditions of temperature, pressure and gas hourly space velocity include at least one of a temperature within a range of from 200° C. to 450° C., a pressure within a range of from 200 psig (1.38 MPa) to 4,000 psig (24.58 MPa) or a gas hourly space velocity is within a range of 300 hr$^{-1}$ to 25,000 hr$^{-1}$.

5. The process of claim 1, wherein the mixture of hydrogen and carbon monoxide has a ratio of hydrogen to carbon monoxide within a range of from 10:1 to 1:10.

6. The process of claim 1, wherein $M_1$ is a combination of cobalt and palladium, cobalt and rhodium, aluminum and rhodium, cobalt and aluminum, copper and cobalt, and zinc and cobalt, and y is 6.

7. The process of claim 1, wherein the mixture of carbon monoxide and hydrogen further comprises an amount of an olefin.

8. The process of claim 7, wherein the olefin is ethylene.

* * * * *